United States Patent [19]
Lilienfeld

[11] Patent Number: 6,055,052
[45] Date of Patent: Apr. 25, 2000

[54] SYSTEM FOR, AND METHOD OF, MONITORING AIRBORNE PARTICULATE, INCLUDING PARTICULATE OF THE $PM_{2.5}$ CLASS

[75] Inventor: Pedro Lilienfeld, Lexington, Mass.

[73] Assignee: MIE Corporation, Bedford, Mass.

[21] Appl. No.: 09/013,146

[22] Filed: Jan. 26, 1998

[51] Int. Cl.$^7$ .......................... G01N 21/00; G01N 15/02; G01N 15/06

[52] U.S. Cl. .......................... 356/338; 356/336; 356/335; 356/339; 356/340; 356/337; 250/574

[58] Field of Search .................. 356/336, 338, 356/335, 337, 340, 339; 250/574, 573, 575

[56] References Cited

U.S. PATENT DOCUMENTS

| | | | |
|---|---|---|---|
| 3,713,743 | 1/1973 | Simms | 356/208 |
| 3,797,937 | 3/1974 | Shofner | 356/102 |
| 3,953,127 | 4/1976 | Ahlquist et al. | 356/103 |
| 4,017,186 | 4/1977 | Shofner et al. | 356/103 |
| 4,017,193 | 4/1977 | Loiterman | 356/206 |
| 4,348,111 | 9/1982 | Goulas et al. | 356/336 |
| 4,482,247 | 11/1984 | Meltz et al. | 356/343 |
| 4,541,719 | 9/1985 | Wyatt | 356/343 |
| 4,689,052 | 8/1987 | Ogren et al. | 55/17 |
| 5,565,984 | 10/1996 | Girvin | 356/338 |
| 5,751,423 | 5/1998 | Traina et al. | 356/338 |
| 5,831,730 | 11/1998 | Traina et al. | 356/338 |

OTHER PUBLICATIONS

Ahlquist, N.C. et. al., "Measurement of the Wavelength Dependence of Atmospheric Extinction Due to Scatter," *Atmospheric Environment* Pergamon Press 1969, vol. 3., pp. 551–564.

Angstrom, A., "On the Atmospheric Transmission on Sun Radiation. II.," Reprinted from *Geografiska Annaler*, vol. 12, (1930), pp. 130–159.

Charlson, R.J., "Multiwavelength Nephelometer Measurements in Los Angeles Smog Aerosol," Reprinted from *Journal of Colloid and Interface Science*, vol. 39, No. 1, Apr., 1972, pp. 240–265.

Covert, D.S., et. al., "A Study of the Relationship of Chemical Composition and Humidity to Light Scattering by Aerosols," *Journal of Applied Meteorology*, vol. 11, Sep. 1972, pp. 968–976.

Horvath, H., "The influence of the wavelength dependent extinction coefficient of the atmospheric aerosol on visibility and its measurement," *American Industrial Hygiene Association* (41) Oct., 1980, pp. 748–757.

Solly, I., et. al., "Mass Size Distrbutions of Humidified Atmospheric Aerosols and of Their Untreated Precursors,"*J. Aerosol Science*, vol. 20, No. 8, 1989, pp. 1151–1153.

Waggoner, A.P., et. al., "Preliminary Communication—Comparison of Fine Particle Mass Concentration and Light Scattering Extinction in Ambient Aerosol," *Atmospheric Environmental*, vol. 14, pp. 623–626.

Wilson, W.E., "A Real–Time Monitor for Volatile Fine Paticulate Matter," AAAR '97, *Abstracts, Sixteenth Annual Conference*, Oct. 13–17, 1997, Renaissance Denver Hotel, Denver, Colorado, p. 39.

*Primary Examiner*—Robert H. Kim
*Assistant Examiner*—Roy M. Punnoose
*Attorney, Agent, or Firm*—Hale and Dorr LLP

[57] ABSTRACT

System for, and method of, monitoring airborne particulate, including particulate of the $PM_{2.5}$ class. The system for monitoring airborne particulate includes an optical sensor to measure size characteristics of sampled airborne particulate and a humidity sensor to measure relative humidity. An adjusted airborne concentration value is then produced in response to the measured size characteristics and to the humidity measurement. According to one embodiment the optical sensor is implemented as a multi-wavelength nephelometer, e.g., two-wavelength nephelometer. According to another embodiment the humidity sensor is placed relatively near the optical sensing region and makes a relative humidity measurement.

22 Claims, 7 Drawing Sheets

TYPICAL AMBIENT FINE PARTICULATES SIZE DISTRIBUTION AT HIGH AND LOW HUMIDITIES

SYSTEM FOR, AND METHOD OF, MONITORING AIRBORNE PARTICULATE, INCLUDING PARTICULATE OF THE $PM_{2.5}$ CLASS

BACKGROUND OF THE INVENTION

1. Field of the Invention

This invention relates to environmental monitoring and, more particularly, to the monitoring of fine particulate of the $PM_{2.5}$ class.

2. Discussion of Related Art

Over the past quarter of a century, government regulations concerning ambient air quality have evolved towards monitoring and regulating ever smaller particles, from the so-called "total suspended particulate" concept, to the $PM_{10}$ class, to the "fine particulate" known as $PM_{2.5}$.

Among other things, the regulations specify a "reference method" (FRM) to monitor, or measure, the amount of airborne particulate matter in air. The reference method has largely remained unchanged. Typically, the method involves sampling air with particle collection on a filter, combined with gravimetric evaluation of the collected mass. Though this method is responsible for much of the relevant recorded data, it has many drawbacks:

1. It's labor intensive and thus not compatible with long-term continuous unattended operation.

2. It provides time-delayed information and is thus incapable of providing real-time measurements.

3. It's subject to both intrinsic measurement ambiguities as well as operational problems.

Concerning drawback (3), the intrinsic measurement ambiguities result when sampling chemically reactive and/or physically unstable aerosols. Such particles, after their capture on the filter, may evaporate, react, or otherwise be altered with respect to their original airborne condition. These effects are further influenced by the design idiosyncrasies of the FRM sampling device, such as the design's flow velocities, filter structure and composition, internal surface characteristics, wall temperatures and their gradients, etc. Such factors may play a role in influencing the fate of the sampled particulate, even before they are subjected to the required sample conditioning procedures, which may involve exposing the collected sample to a controlled humidity and temperature environment to remove accreted liquid water.

Since the 1970s, two types of quasi-continuous, quasi-real-time ambient particulate monitoring devices have been granted "equivalence status" with respect to the filter/gravimetric reference method: filter tape/beta radiation attenuation mass monitors, and the tapered element oscillating mass monitor (TEOM). (Equivalence status permits these devices to be used as a substitute for a FRM device) Both classes of instruments rely on particle collection by filtration, but each uses a different method of sensing the mass of the collected particulate. The former uses the attenuation of beta rays to quantify that mass, whereas the latter relies on sensing the change in the natural resonant frequency of an oscillating body to which a particle collection filter cartridge is attached. The above-mentioned instruments measure cumulative particulate mass and for typical ambient particulate concentrations require sampling periods of the order of one hour to achieve the necessary measurement sensitivity.

These two classes of quasi-continuous particulate mass monitors suffer from the same intrinsic problems as the reference sampling method. That is, they are based on filtration that may affect the integrity of the particles with respect to their airborne state. Furthermore, to preclude errors resulting from water accretion on particles at high humidity levels, these instruments rely on heating of the sample stream. This method of water removal, however, has been found to affect other volatile particle species of interest. See Obeidi, F. and Eatough, D. J., *A Real-Time Monitor for Volatile Fine Particulate Matter*, paper presented at 16th Annual Conference of the AAAR, Oct. 13–17, 1997, p. 39. Similar problems are likely to affect water trapping approaches, such as diffusion drying.

All of the above-mentioned mechanisms that affect the validity of ambient particulate monitoring are especially noticeable in the case of fine particles, also called the accumulation mode. This is so, because these particles are predominantly the result of condensation and photochemical processes. These are inherently unstable aerosols, as opposed to the coarse mode which is constituted principally by aerosolized soil grains and other mechanically generated particles. Thus, the validity of any measurements resulting from conventional devices may be considered suspect as the particles may be significantly affected by the measuring devices.

Thus, there is a need for an in situ technique, and corresponding system, to continuously monitor ambient fine particles, ideally in real-time. There is also a need for a system and technique that can monitor particles without affecting any of the particle species. There is yet another need for a system and technique to monitor particles in a manner that is capable of discriminating against liquid water-caused particle growth. All of the above needs are particularly acute for the measurement of fine particulate of the $PM_{2.5}$ class.

SUMMARY

It is an object of the invention to provide a system for, and method of, addressing the above needs.

An exemplary embodiment of the invention provides an optical sensor to measure size characteristics of sampled airborne particulate and a humidity sensor to measure relative humidity. An adjusted airborne concentration value is then produced in response to the measured size characteristics and to the humidity measurement.

According to one aspect of the invention the optical sensor is implemented as a multi-wavelength nephelometer. According to another aspect of the invention, the humidity sensor is placed relatively near the optical sensing region and makes a relative humidity measurement.

An exemplary method optically senses an air sample to determine size characteristics of airborne particulate in the air sample, and measure relative humidity. A concentration of airborne particulate is then calculated as function of the size characteristics and the humidity measurement.

DETAILED DESCRIPTION

Figure 1:
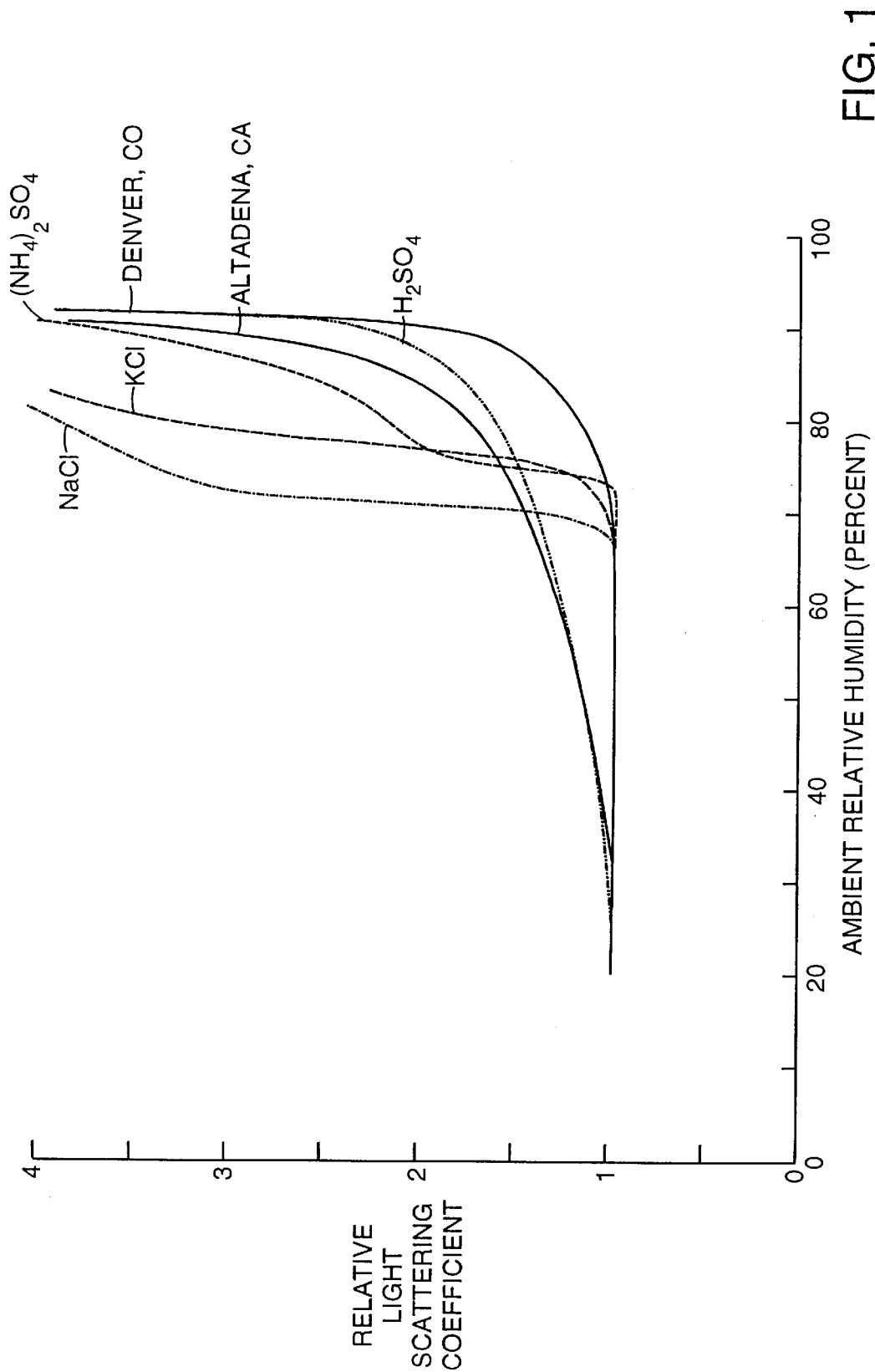
FIG. 1 is a graph illustrating exemplary relationships between relative light scattering coefficients and ambient relative humidity.

An exemplary embodiment of the invention senses concentrations of airborne particulate in a non-invasive manner. In particular, optical sensing of particulate determines certain characteristics of particulate size, such as the median diameter of the sampled particulate. Humidity is measured and the measurement is used by corresponding correction algorithms to cancel the effects of water accretion. Thus, no drying techniques are employed to the sampled air, which might otherwise compromise the validity of the measurements. This is particularly advantageous for monitoring particulate of the class corresponding to $PM_{2.5}$, as these particles often include unstable aerosols.

Nephelometry is the measurement of the scattering irradiance due to airborne particles. In the past, it has been applied to the monitoring of ambient aerosols for visibility studies. In such arrangements, a single-wavelength measurement is performed with light typically, but not exclusively, at a wavelength in the vicinity of 550 nm. There is no correction for humidity. It has also been used for real-time monitoring of particulate mass concentration in experimental contexts. In these cases, aerosol mass concentration measurements use nephelometry based on filter/gravimetric calibration with a test dust (or liquid particles) whose physical properties are representative of the particle population to be monitored. In the absence of particle size information, however, nephelometry for particulate mass concentration measurements has remained a surrogate method; that is, nephelometry is used in this context only as an auxiliary to the standard filter/gravimetric technique. In this surrogate case, as opposed to visibility monitoring, water accreted on the particles at high ambient relative humidities is usually eliminated by heating the sampled air stream, to preclude errors resulting from water induced particle growth. See Waggoner, A. P. and Weiss, R. E., *Comparison of Fine Particle Mass Concentration and Light Scattering Extinction in Ambient Aerosol*, 14 ATMOS. ENVIRON. 623–626 (1980)

Nephelometry, or light scattering photometry, has the following significant advantages with respect to filter collection based particulate sensing methods:

1. Sensing has immaterial contact with the particulate matter and thus immaterially affects the physical or chemical properties of the aerosol.

2. Detection and measurement are performed in real-time and independently of sampling flow rate.

3. Detection sensitivity is superior to any other sensing method.

4. It's capable of operation without attention or maintenance for extended periods of time.

5. It has relatively low equipment cost, both capital and operational.

The relevant aspects of the $PM_{2.5}$ population are (a) mass median diameter of 0.3 to 1.0 $\mu$m, (b) average density of 2 g/cm3, (c) log-normal size distribution function, (d) geometric standard deviation (of size distribution) of 2, and (e) average refractive index of 1.50 to 1.55.

The correlation of nephelometry to filter-based mass concentration measurements depends on the invariance of the above-cited physical properties of ambient particulate matter. If these properties remain constant, the relationship between the nephelometer measurements and mass concentration remains constant. The response is linear up to the onset of multiple scattering non-linearity, which occurs only at concentrations that are many orders of magnitude over ambient levels. Thus, the exemplary nephelometric arrangements described below should suffice as an equivalent device to the FRM.

a. Nephelometry to Determine Particle Size

The scattering coefficient of ambient aerosols is a function of the wavelength of the light used to perform the scattering measurement. That dependence is, in turn, a function of the size of the particles with respect to that wavelength. For particles that are much smaller than the wavelength, the scattering coefficient varies as the inverse fourth power of the wavelength. For particles whose size is much larger than the wavelength of the light used to illuminate them, the scattering coefficient is independent of wavelength. For particles whose size is comparable to the wavelength of the illuminating beam, the wavelength dependence of the scattering coefficient follows an inverse 1.5 to 2.5 power law. This last case is the most representative of using nephelometry on the fine particle population, using a source in the customary range of wavelengths of 400 to 1000 nm. The magnitude of this exponent (called the Ångstrom coefficient) is, in turn, a function of the size of the particles. For an aerosol with a specific size distribution function (e.g., log-normal with a given geometric standard deviation), that wavelength dependence is a function of the volume median diameter of the particle population. These relationships are known. See Charlson, R. J. et al, *Multiwavelength Nephelometer Measurements in Los Angeles Smog Aerosol*, 39 J. COLLOID AND INTERFACE SCI., 240–265 (1972)

From the above-described wavelength dependence of the scattering coefficient, it is possible to determine the volume median diameter of the $PM_{2.5}$ particle population. In particular, by performing concurrent, or virtually concurrent, measurements of the scattering at more than one wavelength, the known interrelationships may be used to determine the volume median diameter. See Charlson, R. J. et al, supra.

b. The Water/Volatility Problem

As ambient relative humidities rise above about 65 to 70%, fine particulate tend to grow very rapidly as a result of liquid water accretion. The magnitude of this humidity induced growth depends on the composition of the particles. This effect is illustrated in FIG. 1. For $PM_{2.5}$ monitoring, which monitors mass concentrations, the accreted water is an interference to be eliminated, since only the core particle contribution is to be quantified.

Figure 2:
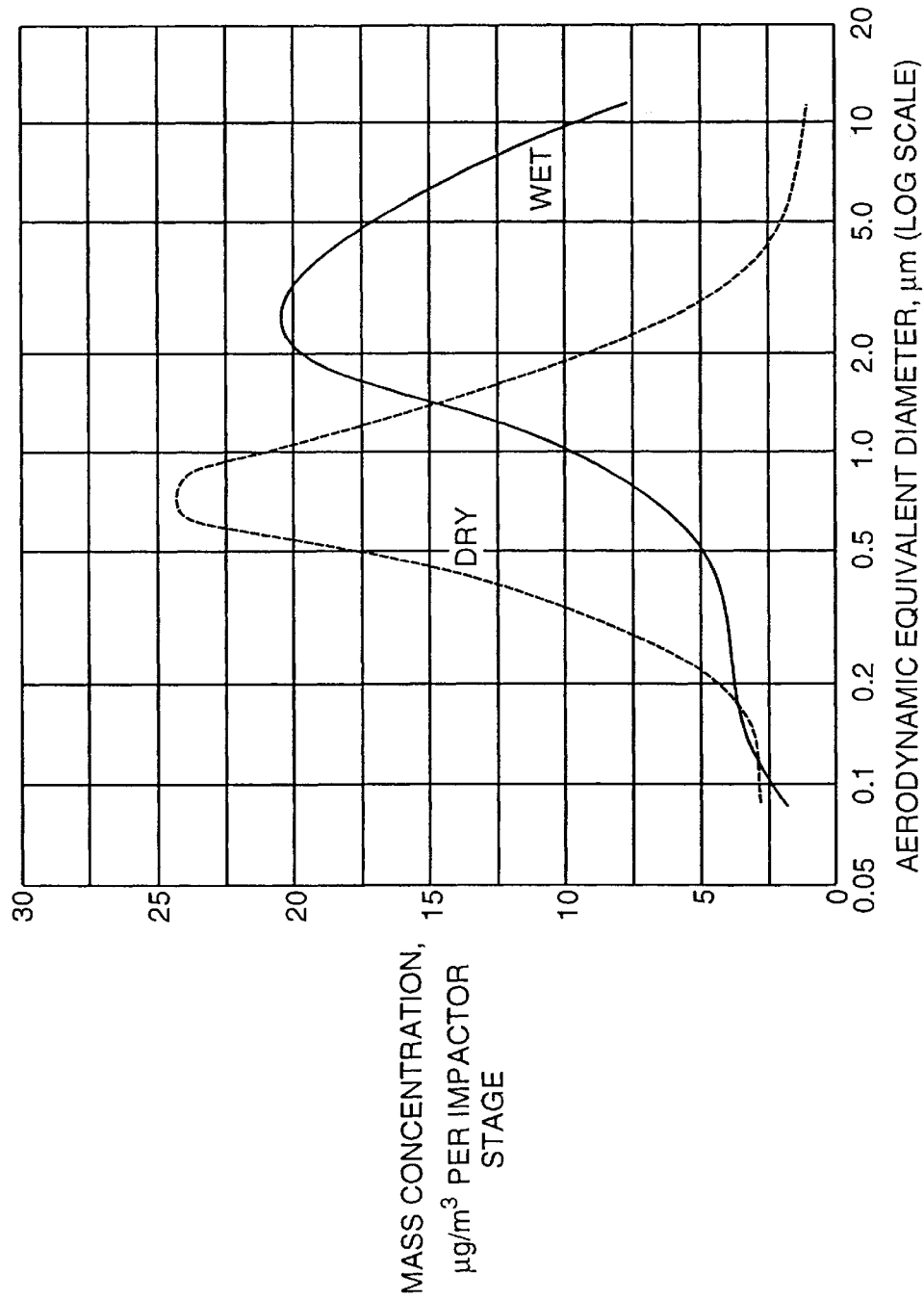
FIG. 2 is a graph illustrating an exemplary relationship between mass concentration and aerodynamic equivalent diameter.

If high humidity (e.g., over 70%) is accompanied by particle growth, that size increment may be safely attributed to the interfering effect of liquid water accretion. FIG. 2 illustrates this effect by showing the measured particle size distributions of ambient fine particulate near Vienna for both dry and humid conditions.

To this end, an exemplary embodiment of the invention combines multi-wavelength nephelometry (e.g., two-wavelength) and relative humidity sensing. By identifying the combination of high humidity and particle growth, the effects of water accretion may be corrected and canceled. The salient advantage of this method is that the integrity of the particles remains unaffected; thus, volatile compounds, if present, are preserved unaltered.

A shift towards larger particles without concomitant high humidity would be attributable to other factors, for example, to the inclusion of a small-particle tail of the distribution of wind blown desert sand carried over long distances. Alternatively, high humidity without significant particle growth would be indicative of hydrophobic particulate matter.

c. Particular Arrangements

Figure 3:
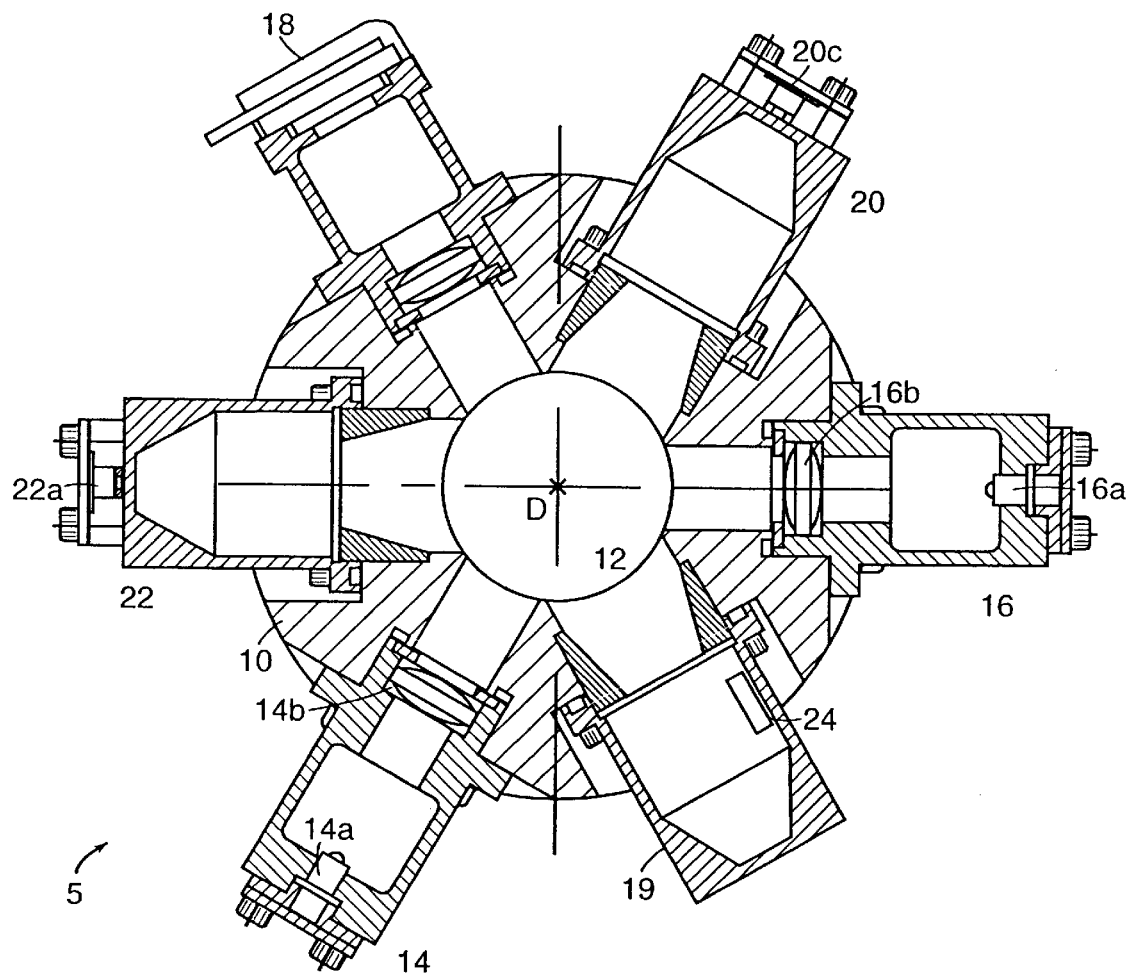
FIG. 3 is a transverse, cross-sectional view of an exemplary optical sensing arrangement for determining the size of particulate.

An exemplary sensing configuration of a two-wavelength nephelometer is depicted in FIG. 3 as a transverse, cross-sectional view. The configuration 5 includes housing 10 through which passes a central flow duct 12. The housing 10 is typically manufactured of anodized aluminum and coated internally with an antireflectant paint. The flow duct 12 has a typical inner diameter ranging from one to several centimeters. The sampled air stream passes through the central flow duct 12, perpendicularly to the plane of the paper. The illumination beams are provided by two light sources 14 and 16, each having light emitting diodes (LEDs) 14a and 16a and collimating optics 14b and 16b. The axes of illumination of these two LEDs are symmetrically positioned with respect to the axis D of the common scattering detector 18, which detects scattered light in the sensing region. Light trap 19 provides a dark background to facilitate such detection. The scattering angle for both sources is symmetric with respect to the common detection axis, defined by the detector 18 and trap 19, for example, a scattering angle of 60°. Each of the source beams traverses the sensing region within the flow duct 12 after which the unscattered portion of these beams enter their respective light trapping cavities 20 and 22. At the end of each of these two cavities there is a beam detector 20a and 22a that serves as reference in a feed-back control circuit (not shown) that maintains a constant light output from a corresponding one of the two LED sources 14a and 16a.

The two LED sources emit at different wavelengths. For example, the first wavelength preferably emits light at a wavelength chosen from the range of about 550 nm to about 600 nm. The second wavelength preferably emits light at a wavelength chosen from the range of about 880 nm to about 950 nm. Preferably, the LEDs are high power, for example, from 5 to 15 mW, and relatively narrowly collimated, for example, about 10°. Typical LEDs of this type are gallium-aluminum-arsenide domed-lens emitters. One embodiment, for example, uses a 600 nm LED and a 880 nm LED. Source wavelengths can be other than 880 and 600 nm, provided they are in the near infrared and/or visible bands.

Each LED's light causes scattered light at a corresponding wavelength, which is sensed by the common scattering detector 18. Control logic (not shown) causes the activation of the two light sources 14 and 16 to rapidly alternate and pulse. The control logic also causes the synchronous gating at the detector 18 effectively resulting in two independent signal channels, one for each wavelength. Typical pulse frequencies are in the range of a few per second to several hundred per second, depending on the speed of response of the detector used, and its associated circuitry.

Figure 4:
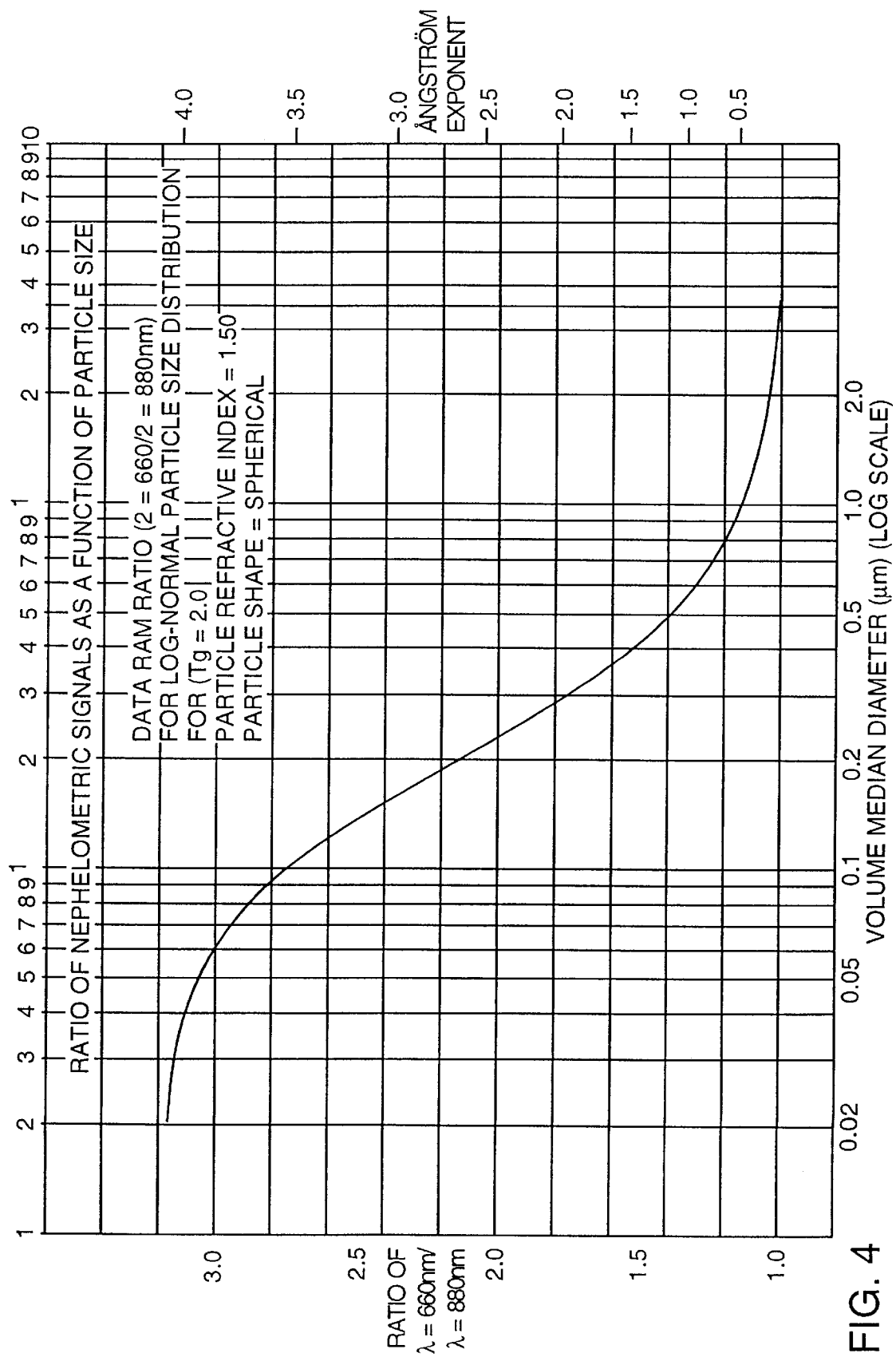
FIG. 4 is a graph illustrating an exemplary relationship between the ratio of detected light of the arrangement of FIG. 3 relative to the volume median diameter of the particulate matter being sensed.

The ratio of the magnitudes of the two signals detected by common detector 18 (i.e., one signal for each wavelength source) is a function of the volume median diameter of the fine particle population. An exemplary function, corresponding to the 600 and 880 nm sources, is illustrated in FIG. 4. Thus, the ratio may be used to determine volume median diameter of the particulate matter.

The magnitude of either of the two signals, in combination with the volume median particle diameter determined as described above, and based on the narrow variability of the average density of these particles, yields the mass concentration, i.e., the $PM_{2.5}$ concentration.

A relative humidity sensor 24 provides the corresponding information to correct the mass concentration value when the ambient relative humidity exceeds a known value (typically 70%). As shown, sensor 24 is placed relatively near the region where the particulate is optically sensed (the "optical sensing region"). An exemplary embodiment positions the sensor in the sample stream, e.g., in direct flow contact with air duct 12, so that the humidity measurement more accurately reflects the conditions under which the particles are optically sensed. Thus, the humidity measurement and the median diameter measurement are both inputs to a correction algorithm that provides a humidity-adjusted concentration value.

As shown in FIG. 1, the correction algorithm may be with respect to particular matter, e.g., NaCl, or with respect to a particular location, e.g., Denver, Colo. The algorithm may be implemented as a look-up table, or as an explicit function, with the humidity as an input and a correction factor as an output. The correction factor, in turn, may be derived as a result of the observed changes in scattering coefficient as a function of humidity. This correction algorithm may be based on an average of the observed increase in scattering coefficient as a function of humidity (for example, based on the average of the curves of FIG. 1). Alternatively, the humidity correction algorithm may be based on local measurements of the effects of humidity on scattering coefficient.

The exemplary particle size and humidity sensing apparatus may be utilized in many forms. Two preferred forms are (a) as a portable instrument and (b) combined with a federal reference method (FRM) filter sampler.

Figure 5:
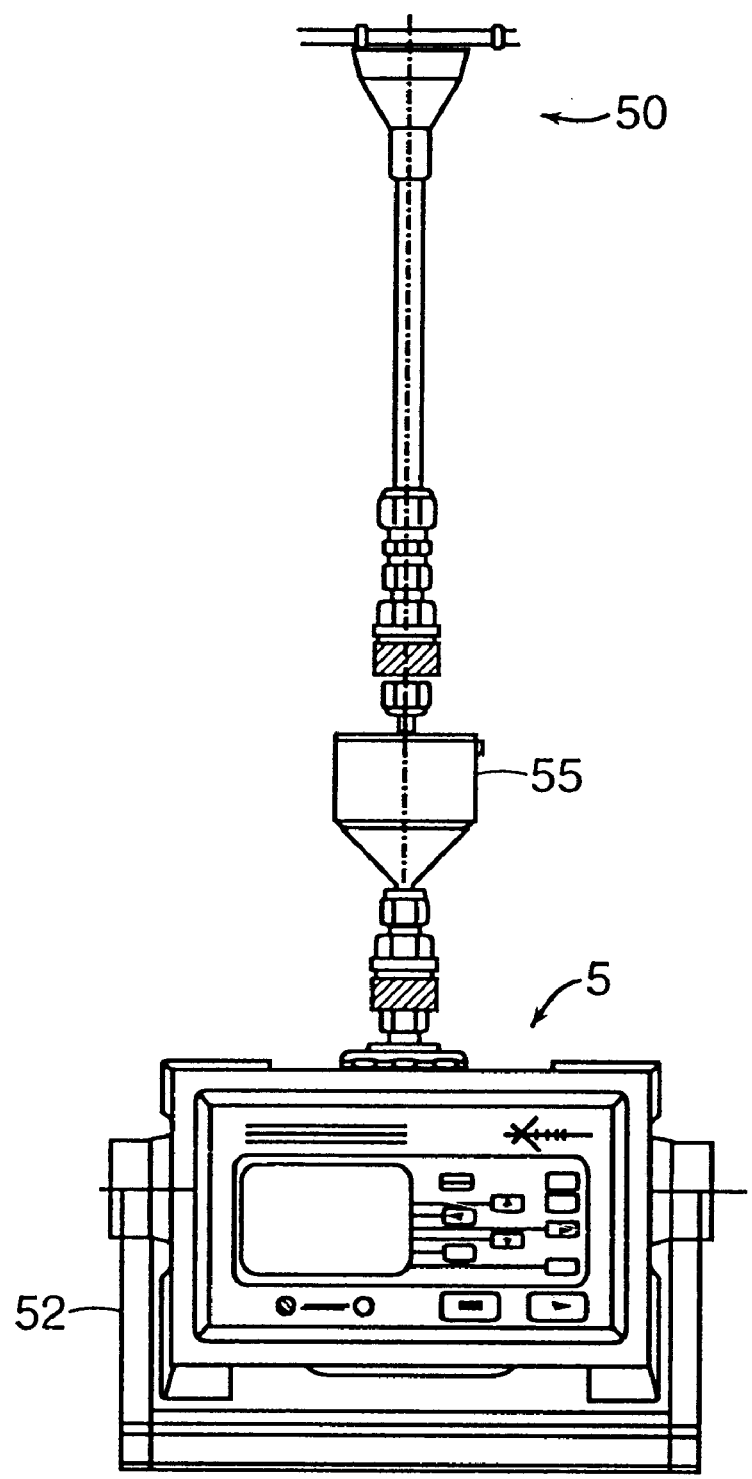
FIG. 5 is a front view of an exemplary embodiment of the invention.

The portable version will be similar to MIE model DR-2000, but will substitute the above-described two-wavelength nephelometer for the single wavelength nephelometer used by the DR-2000. In addition, it will also include the humidity sensor, and correction and computation algorithms described above as software logic within its control processor 52. The portable version will operate typically at a flow rate of 2 liters per minute and will utilize the omnidirectional sampling inlet 50 and the 2.5 $\mu$m in-line impactor 55 that are presently provided as optional accessories of the model DR-2000, as shown in FIG. 5. The salient advantages of this version are its compactness, portability, and relatively low cost.

Figure 6:
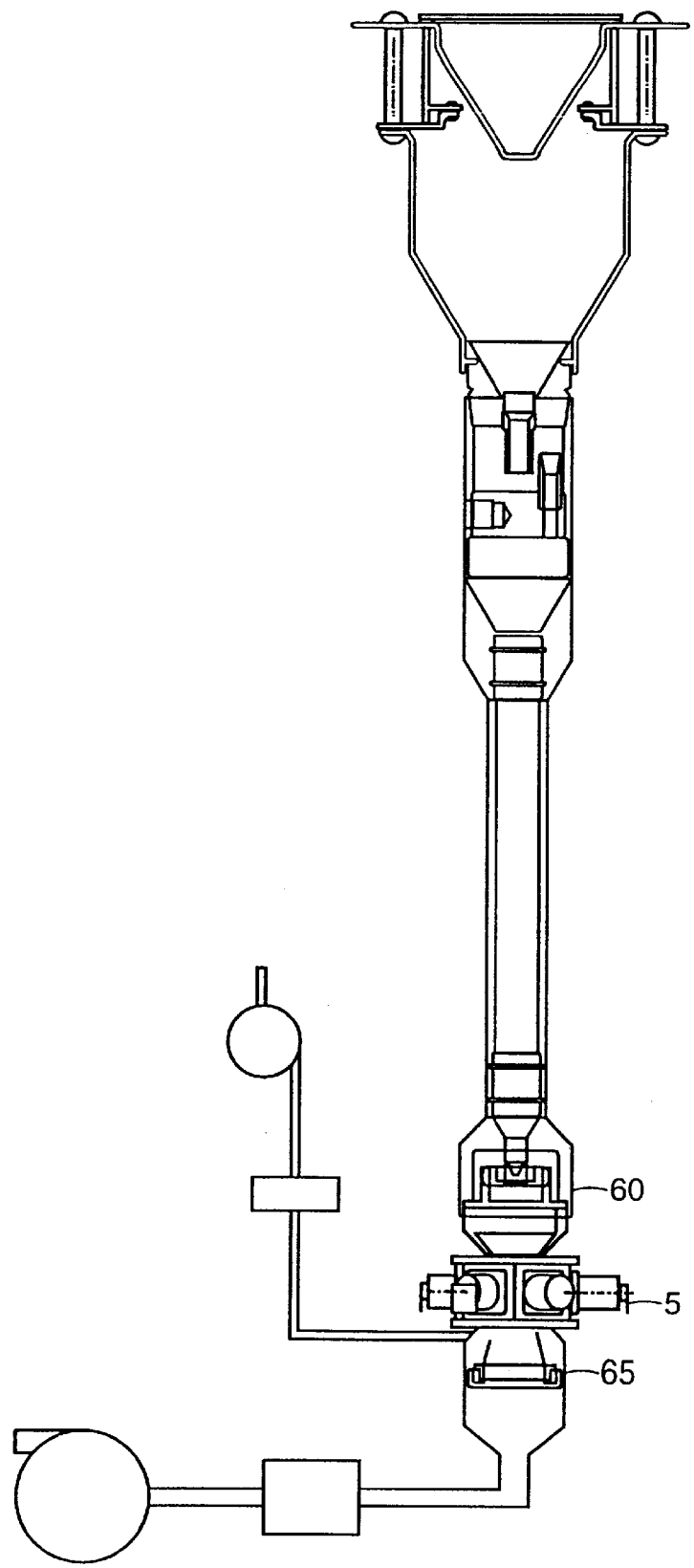
FIG. 6 is a side-elevation view verify of an exemplary embodiment of the invention (version combined with an FRM device)
Figure 7:
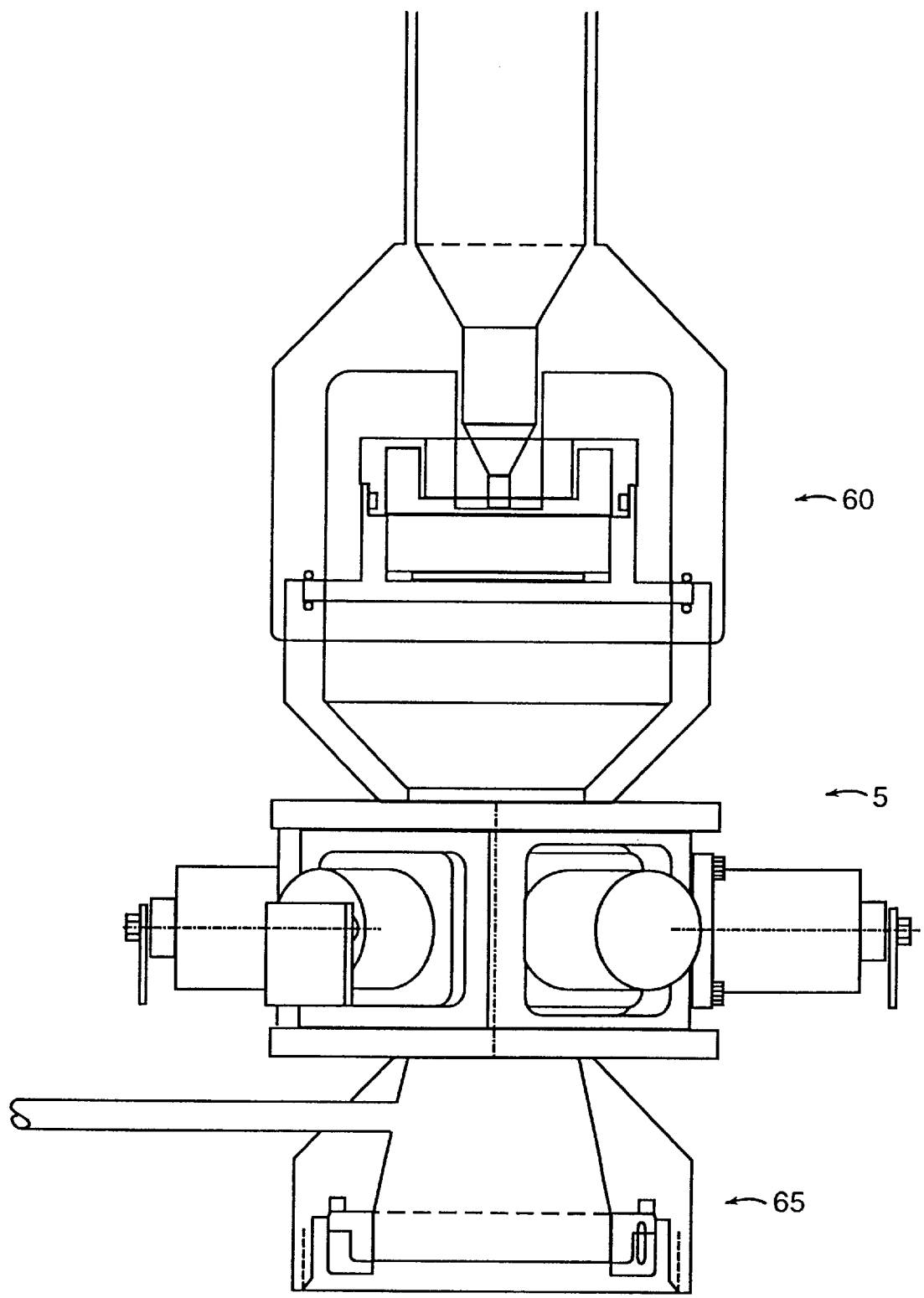
FIG. 7 is an enlarged view of a portion of the embodiment of FIG. 6, particularly showing an optical sensing arrangement in relation to an impactor and filter holder used in conjunction with an FRM device.

The second version will consist of a modification of the FRM sampler for $PM_{2.5}$. (The FRM for $PM_{2.5}$, in essence, is a filter/gravimetric sampler operating at a flowrate of 16.67 liters per minute (1 m3 per hour). For more details, see CFR 40, Part 50, Appendix L, 62 Fed. Reg. 138 (1997).) The modification of the FRM includes the incorporation of the optical sensing configuration 5, described above, within a flow duct of the FRM downstream of the 2.5 $\mu$m impactor and upstream of the filter collection stage. In particular, the optical sensing configuration 5 is placed between impactor 60 and filter holder 65. This configuration is depicted generally in FIG. 6 and in enlarged view in FIG. 7.

The incorporation of the two-wavelength nephelometric sensing stage 5 and humidity sensor within the FRM provides the following advantages:

1. By sampling the ambient environment at the same flow rate, and by performing the 2.5 μm particle size precollection within the same geometry as the FRM, all possible particle sampling, transport, and size separation discrepancies with respect to the FRM are precluded. This provides consistency of air sampling and particle size discrimination with respect to the FRM.

2. Direct gravimetric calibration of the nephelometric sensing system can be accomplished by using the filter collection stage of the modified FRM.

3. Existing FRM units may be retro-fitted to incorporate real-time monitoring capabilities.

To preserve the continuous unattended monitoring advantage of the nephelometric sensing, the filter 65 of the FRM can be replaced by a non-clogging flow restrictor whose pressure drop equals that of the filter.

Automatic zeroing of the nephelometric sensing system will be accomplished similarly to the process used in the model DR-2000. In particular, filtered particle-free air will be injected downstream of the sensing stage. A programmed sequence, e.g., every 24 hours, will shut off the main sampling pump and activate a small diaphragm pump to cause it to feed filtered air to purge the optical sensing chamber. Concurrently, the scattering detector will sense the optical backgrounds at the two wavelengths and electronically register the measurements so that they may be subsequently subtracted from the measured signals during normal air sampling.

There are two calibration procedures. The first calibration procedure is an absolute scattering coefficient response determination. This is required to obtain the appropriate response relationship between the two signal channels, one for each wavelength. This is required because the relative source outputs 14a and 16a as well as the spectral sensitivity of the common detector 18 may vary from system to system. The scattering coefficient ratio calibration is performed using a gas (e.g., Freon-12 or equivalent) with known scattering coefficient at a given wavelength. Since the wavelength dependence of that coefficient is known precisely for gases it is straightforward to normalize the response of the two signal channels.

The second type of calibration is with respect to a reference mass concentration measurement. This will be accomplished by means of collocated monitoring of either laboratory or ambient aerosols using a filter gravimetric reference. In the case of ambient particulate calibration, one or more FRMs would be used (either separately or as a part of a combined system of FIGS. 6 and 7). For the mass concentration calibration, only one of the two signal channel needs to be used. The other would be designed to track automatically at a constant ratio as established by the scattering coefficient normalization, explained above.

Having described an exemplary embodiment, it should be apparent to persons of ordinary skill in the art that changes may be made to the embodiment described without departing from the spirit and scope of the invention. For example, though the placement of the humidity sensor in close proximity to the optical sensing apparatus provides certain advantages, it is possible that the humidity measurement may be taken elsewhere and scaled according to a correction factor that compensates for the two environments. Likewise, other optical sensing arrangements and devices are foreseeable, and other mechanisms may be used for particle sizing.

What is claimed is:

1. A system for monitoring the amount of airborne particulate, comprising:
   (a) an optical sensor to measure size characteristics of sampled airborne particulate;
   (b) a humidity sensor to measure relative humidity of an air sample; and
   (c) concentration value logic apparatus, responsive to measured size characteristics and to a humidity measurement, for providing an adjusted airborne concentration value.

2. The system of claim 1 wherein the optical sensor is a nephelometer.

3. The system of claim 2 wherein the nephelometer is a multi-wavelength nephelometer.

4. The system of claim 2 wherein the nephelometer is a two wavelength nephelometer.

5. The system of claim 4 wherein the two wavelength nephelometer includes a first light source operating at a wavelength chosen from the range of approximately 550 nm to approximately 600 nm and a second light source operating at a wavelength chosen from the range of approximately 880 nm to about 950 nm.

6. The system of claim 5 wherein the first light source operates at 600 nm and the second light source operates at 880 nm.

7. The system of claim 4 wherein the nephelometer comprises
   a first light source and a second light source, and
   a light detector in optical communication with scattered light caused by the first and second light sources, and
   wherein the system further comprises control logic that activates the first and second light sources in an alternating manner for predefined activation pulse durations.

8. The system of claim 7 wherein the first and second light sources are in symmetrical relationship to the light detector.

9. The system of claim 7 wherein the system includes an air duct through which an air sample to be monitored passes and wherein the first and second light sources and the common light detector are in a radial relationship to a longitudinal axis of the air duct.

10. The system of claim 9 wherein the first and second light sources are disposed in symmetrical radial relationship relative to the longitudinal axis of the air duct.

11. The system of claim 7 wherein the first and second light sources are disposed relative to the light detector so that each defines an approximately 60 degrees scattering angle.

12. The system of claim 4 wherein the two wavelength nephelometer provides a first measurement value from sensing the air sample at a first frequency and a second measurement value from sensing the air sample at a second frequency, and wherein the size characteristics of sampled airborne particulate is determined as a function of the ratio of the first and second measurement values.

13. The system of claim 1 wherein the air sample measured by the humidity sensor is the same as an air sample having the sampled airborne particulate measured by the optical sensor.

14. The system of claim 1 wherein the system defines an optical sensing region wherein an air sample is optically sensed by the optical sensor, the humidity sensor being placed in proximity to the optical sensing region.

15. The system of claim 1 further comprising an FRM device for monitoring particulate of the $PM_{2.5}$ class.

16. The system of claim 15 wherein the FRM device includes an 2.5 µm impactor and a filter holder, the optical sensor being placed between the impactor and filter holder.

17. A method of monitoring airborne particulate, the method comprising the steps of:
   (a) optically sensing an air sample to determine size characteristics of airborne particulate in the air sample;
   (b) measuring relative humidity of an air sample; and
   (c) calculating a concentration of airborne particulate as a function of the size characteristics and a humidity measurement.

18. The method of claim 17 wherein step (a) optically senses the air sample using a multiple wavelength nephelometer.

19. The method of claim 17 wherein step (a) uses a two wavelength nephelometer to determine a median diameter of airborne particulate.

20. The method of claim 19 wherein the median diameter is determined by taking a first measurement of the sample at a first wavelength of light of the nephelometer and by taking a second measurement of the sample at a second wavelength of light of the nephelometer and by forming a ratio of the first measurement and second measurement that is in a functional relationship to the median diameter.

21. The method of claim 18 wherein the nephelometer includes a first light source and second light source and a common light detector in optical communication with scattered light caused by the first and second light sources, and wherein the first and second measurements are taken by alternately controlling the activation of the first and second light sources.

22. The method of claim 17 wherein the optical sensing is performed in an enclosed sensing region and wherein step (b) measures the humidity in the enclosed sensing region.

* * * * *